US012562077B2

(12) United States Patent
Lee

(10) Patent No.: US 12,562,077 B2
(45) Date of Patent: Feb. 24, 2026

(54) METHOD, COMPUTING DEVICE, AND NON-TRANSITORY COMPUTER-READABLE RECORDING MEDIUM TO TRANSLATE AUDIO OF VIDEO INTO SIGN LANGUAGE THROUGH AVATAR

(71) Applicant: LINE Plus Corporation, Seongnam-si (KR)

(72) Inventor: Yunji Lee, Seongnam-si (KR)

(73) Assignee: LINE Plus Corporation, Seongnam-si (KR)

( * ) Notice: Subject to any disclaimer, the term of this patent is extended or adjusted under 35 U.S.C. 154(b) by 476 days.

(21) Appl. No.: 18/147,118

(22) Filed: Dec. 28, 2022

(65) Prior Publication Data

US 2023/0215296 A1      Jul. 6, 2023

(30) Foreign Application Priority Data

Dec. 30, 2021      (KR) ........................ 10-2021-0193128

(51) Int. Cl.
*G09B 21/00*      (2006.01)
*A61B 5/16*      (2006.01)
*G06T 13/40*      (2011.01)
*G06V 40/16*      (2022.01)
*G06V 40/20*      (2022.01)
*G10L 13/00*      (2006.01)
*G10L 15/26*      (2006.01)

(52) U.S. Cl.
CPC ............ *G09B 21/009* (2013.01); *A61B 5/165* (2013.01); *G06T 13/40* (2013.01); *G06V 40/161* (2022.01); *G06V 40/28* (2022.01); *G10L 13/00* (2013.01); *G10L 15/26* (2013.01)

(58) Field of Classification Search
CPC .... G09B 21/009; G06V 40/28; G06V 40/161; A61B 5/165; G06T 13/40; G10L 15/26; G10L 15/25
See application file for complete search history.

(56) References Cited

U.S. PATENT DOCUMENTS

| | | | |
|---|---|---|---|
| 2006/0174315 A1* | 8/2006 | Kim ..................... | H04N 21/435 |
| | | | 725/136 |
| 2014/0171036 A1* | 6/2014 | Simmons ............. | G09B 21/009 |
| | | | 455/414.1 |
| 2017/0277684 A1* | 9/2017 | Dharmarajan Mary ..................... | |
| | | | G10L 13/00 |
| 2020/0294525 A1* | 9/2020 | Santos .................... | G10L 15/26 |

FOREIGN PATENT DOCUMENTS

KR      10-0401262 B1      10/2003

* cited by examiner

*Primary Examiner* — Richemond Dorvil
*Assistant Examiner* — Adam Michael Weaver
(74) *Attorney, Agent, or Firm* — Sughrue Mion, PLLC

(57) ABSTRACT

A sign language translation method performed by at least one processor includes setting a sign language translation avatar in a video call, translating speech of at least one speaker into sign language during the video call, and displaying the sign language through the sign language translation avatar during the video call.

14 Claims, 11 Drawing Sheets

FIG. 3

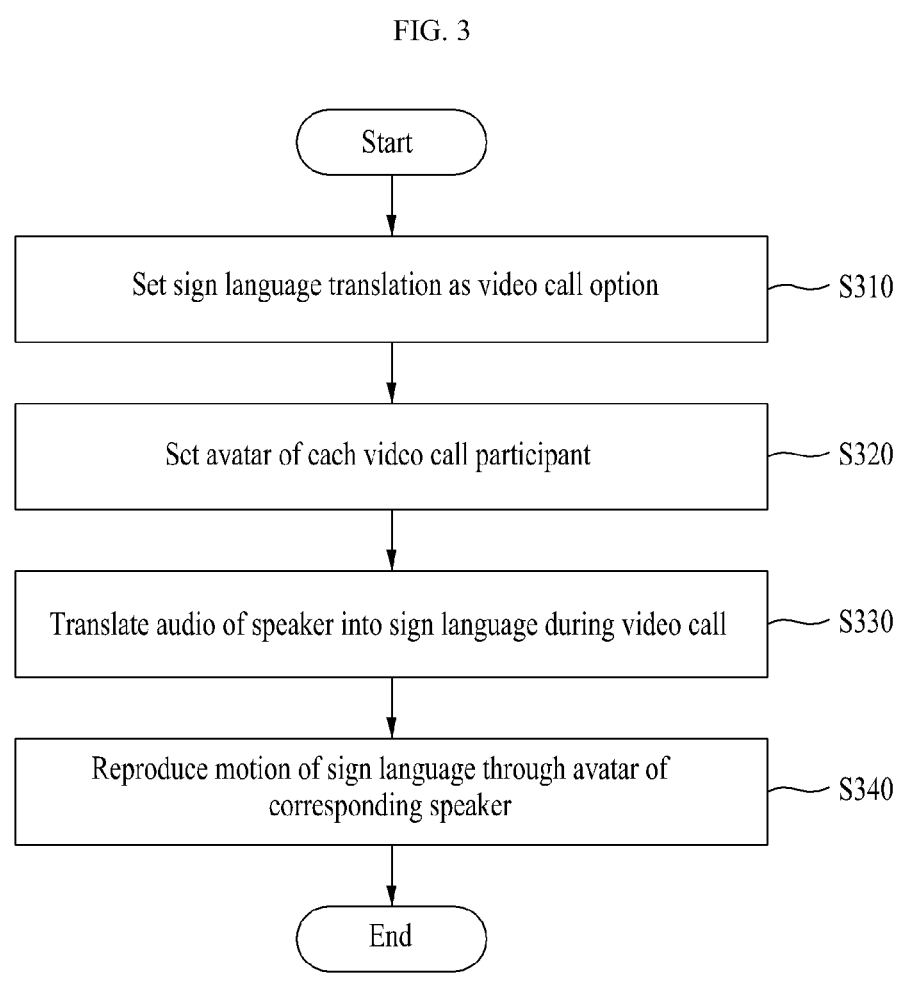

```
                        ┌─────────────┐
                        │    Start    │
                        └─────────────┘
                               │
                               ▼
┌──────────────────────────────────────────────────────┐
│      Set sign language translation as video call option│ ──── S310
└──────────────────────────────────────────────────────┘
                               │
                               ▼
┌──────────────────────────────────────────────────────┐
│          Set avatar of each video call participant     │ ──── S320
└──────────────────────────────────────────────────────┘
                               │
                               ▼
┌──────────────────────────────────────────────────────┐
│ Translate audio of speaker into sign language during video call│ ──── S330
└──────────────────────────────────────────────────────┘
                               │
                               ▼
┌──────────────────────────────────────────────────────┐
│      Reproduce motion of sign language through avatar of│
│                  corresponding speaker                 │ ──── S340
└──────────────────────────────────────────────────────┘
                               │
                               ▼
                        ┌─────────────┐
                        │     End     │
                        └─────────────┘
```

METHOD, COMPUTING DEVICE, AND NON-TRANSITORY COMPUTER-READABLE RECORDING MEDIUM TO TRANSLATE AUDIO OF VIDEO INTO SIGN LANGUAGE THROUGH AVATAR

CROSS-REFERENCE TO RELATED APPLICATION(S)

This application is based on and claims priority under 35 U.S.C. § 119 to Korean Patent Application No. 10-2021-0193128, filed Dec. 30, 2021 in the Korean Intellectual Property Office (KIPO), the disclosure of which is incorporated herein by reference in its entirety.

BACKGROUND

1. Field

Example embodiments of the present disclosure relate to technology for providing a sign language translation service.

2. Description of Related Art

A current communication device provides a variety of services, such as a wireless Internet service, a terrestrial/satellite broadcasting service, etc., in addition to an audio call service or a text service.

In particular, with developments in video compression technology and video restoration technology and with commercialization of a device equipped with a camera, a video call service that enables a call while verifying a face of a counterpart may be provided.

SUMMARY

Example embodiments may translate a call audio into sign language in real time using an avatar during a video call.

Example embodiments may easily identify a speaking entity by providing sign language through an avatar of each speaker.

Example embodiments may analyze a call video or a call audio and may apply a facial expression or emotion of a speaker to a facial expression of an avatar.

Additional aspects will be set forth in part in the description which follows and, in part, will be apparent from the description, or may be learned by practice of the presented embodiments.

According to an aspect of the disclosure, a sign language translation method performed by at least one processor may include setting a sign language translation avatar in a video call, translating speech of at least one speaker into sign language during the video call, and displaying the sign language through the sign language translation avatar during the video call.

The method may further include providing a video call option for selecting sign language translation for each participant of the video call, where the setting is performed based on a selection of the video call option for sign language translation.

The setting may include recognizing a face from a call video of at least one participant of the video call, generating a first avatar based on the recognized face, and setting the first avatar as the sign language translation avatar.

The translating the speech of the at least one speaker into sign language may include analyzing an emotional state of the at least one speaker from at least one of a call video and a call audio of the at least one speaker, where the method may further include representing the emotional state of the at least one speaker with a facial expression or a gesture of the sign language translation avatar.

The at least one speaker may include at least two speakers, avatars of the at least two speakers may appear together in the video call, and translating the speech of the at least one speaker into sign language may include translating speech of each of the at least two speakers into sign language when the at least two speakers concurrently speak.

Displaying the sign language may include displaying an avatar video of the at least one speaker to be overlaid on one side of a video call screen on which a call video of the at least one speaker is configured as a single screen.

The method may further include distinguishably displaying a call video of the at least one speaker through a separate display element on a video call screen on which a call video of a participant of the video call is configured as a single screen.

The at least one speaker may include a first speaker and a second speaker, and the method may further include, when the first speaker and the second speaker concurrently speak, displaying a first display element corresponding to the first speaker, displaying a second display element different from the first display element and corresponding to the second speaker, displaying a first avatar corresponding to the first speaker with the first display element, and displaying a second avatar corresponding to the second speaker with the second display element.

The method may further include recognizing sign language in a call video during the video call, and translating the recognized sign language into a text caption or audio.

According to an aspect of the disclosure, a sign language translation method performed by at least one processor may include setting a sign language translation avatar for each character that appears in a video within a video platform, translating speech of at least one speaker into sign language during playback of the video, and displaying the sign language through the sign language translation avatar during playback of the video.

The method may include providing a video call option for selecting sign language translation for each participant of the video, where the setting is performed based on a selection of the video call option for sign language translation.

According to an aspect of the disclosure, a computing device may include a memory storing instructions, and at least one processor configured to execute the instructions to set a sign language translation avatar in a video call, translate speech of at least one speaker into sign language during the video call, and display the sign language through the sign language translation avatar during the video call.

The at least one processor may be further configured to execute the instructions to provide a video call option for selecting sign language translation for each participant of the video call, where the setting of the sign language translation avatar is performed based on a selection of the video call option for sign language translation.

The at least one processor may be further configured to execute the instructions to recognize a face from a call video of at least one participant of the video call, generate a first avatar based on the recognized face, and set the first avatar as the sign language translation avatar.

The at least one processor may be further configured to execute the instructions to analyze an emotional state of the at least one speaker from at least one of a call video and a call audio of the at least one speaker and represent the emotional state of the at least one speaker with a facial expression or a gesture of the sign language translation avatar.

The at least one speaker may include at least two speakers, avatars of the at least two speakers may appear together in the video call, and the at least one processor may be further configured to execute the instructions to translate speech of each of the at least two speakers into sign language when the at least two speakers concurrently speak.

The at least one processor may be further configured to execute the instructions to display an avatar video of the at least one speaker to be overlaid on one side of a video call screen on which a call video of the at least one speaker is configured as a single screen.

The at least one processor may be further configured to execute the instructions to distinguishably display a call video of the at least one speaker through a separate display element on a video call screen on which a call video of a participant of the video call is configured as a single screen.

The at least one speaker may include a first speaker and a second speaker, and the at least one processor may be further configured to execute the instructions to, when the first speaker and the second speaker concurrently speak, display a first display element corresponding to the first speaker, display a second display element different from the first display element and corresponding to the second speaker, display a first avatar corresponding to the first speaker with the first display element, and display a second avatar corresponding to the second speaker with the second display element.

The at least one processor may be further configured to execute the instructions to recognize sign language in a call video during the video call, and translate the recognized sign language into a text caption or audio.

BRIEF DESCRIPTION OF DRAWINGS

The above and other aspects, features, and advantages of certain embodiments of the present disclosure will be more apparent from the following description taken in conjunction with the accompanying drawings, in which:

FIG. 3 is a flowchart illustrating an example of a method performed by a computing device according to an example embodiment;

Figure 1:
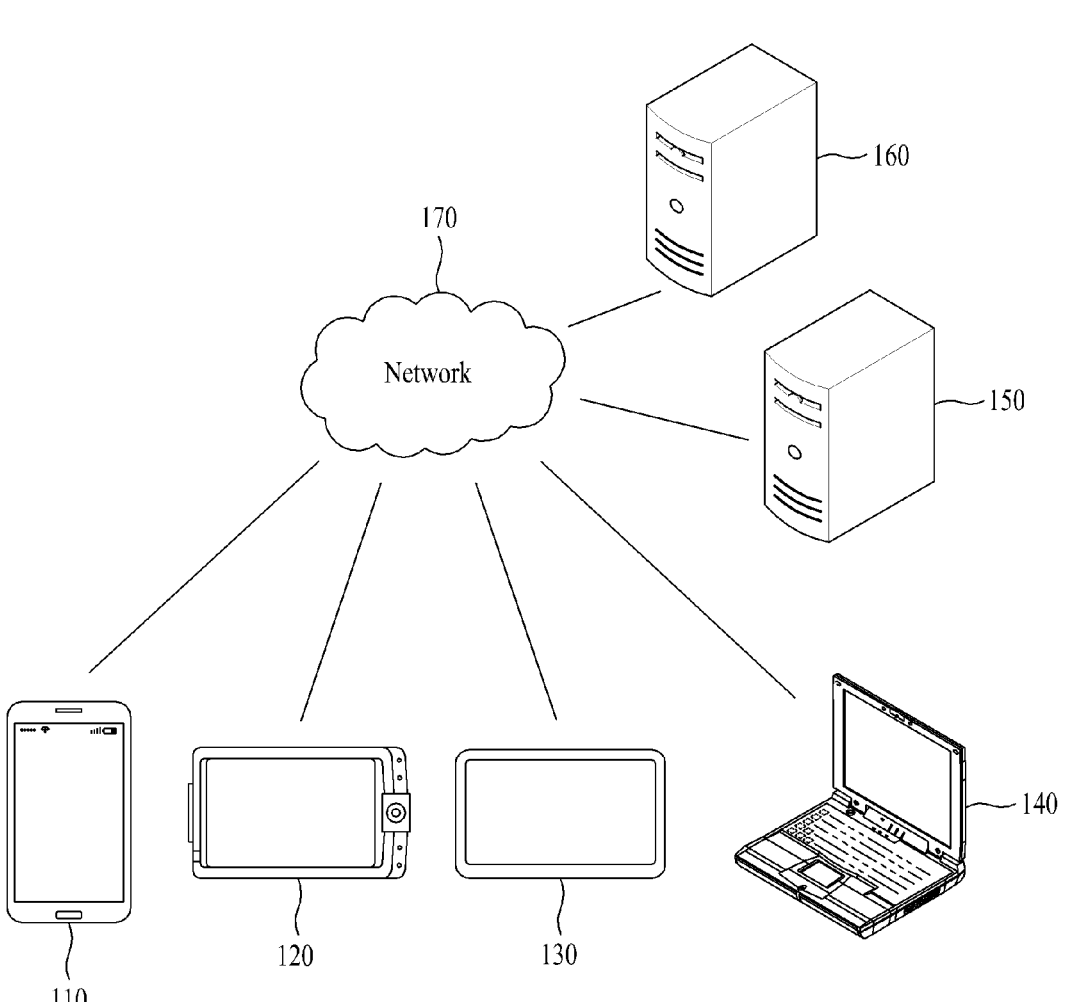
FIG. 1 is a diagram illustrating an example of a network environment according to an example embodiment.

It should be noted that these figures are intended to illustrate the general characteristics of methods and/or structure utilized in certain example embodiments and to supplement the written description provided below. These drawings are not, however, to scale and may not precisely reflect the precise structural or performance characteristics of any given embodiment, and should not be translated as defining or limiting the range of values or properties encompassed by example embodiments.

DETAILED DESCRIPTION

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

One or more example embodiments will be described in detail with reference to the accompanying drawings. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated.

Although the terms "first," "second," "third," etc., may be used herein to describe various elements, components, regions, layers, and/or sections, these elements, components, regions, layers, and/or sections, should not be limited by these terms. These terms are only used to distinguish one element, component, region, layer, or section, from another region, layer, or section. Thus, a first element, component, region, layer, or section, discussed below may be termed a second element, component, region, layer, or section, without departing from the scope of this disclosure.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein translated accordingly. In addition, when an element is referred to as being "between" two elements, the element may be the only element between the two elements, or one or more other intervening elements may be present.

As used herein, the singular forms "a," "an," and "the," are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups, thereof. As used herein, the term "and/or" includes any and all combinations of one or more of the associated listed products. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

Unless otherwise defined, all terms (including technical and scientific terms) used herein have the same meaning as commonly understood by one of ordinary skill in the art to which example embodiments belong. Terms, such as those defined in commonly used dictionaries, should be translated as having a meaning that is consistent with their meaning in the context of the relevant art and/or this disclosure, and should not be translated in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed concurrently, or in some cases be performed in reverse order.

Units and/or devices according to one or more example embodiments may be implemented using hardware and/or a combination of hardware and software. For example, hardware devices may be implemented using processing circuitry such as, but not limited to, a processor, central processing unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above.

Examples of program code include both machine code produced by a compiler and higher level program code that is executed using an interpreter.

For example, when a hardware device is a computer processing device (e.g., a processor), CPU, a controller, an ALU, a digital signal processor, a microcomputer, a microprocessor, etc., the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer record medium or device, capable of providing instructions or data to, or being interpreted by, a hardware device. The software also may be distributed over network coupled computer systems so that the software is stored and executed in a distributed fashion. In particular, for example, software and data may be stored by one or more computer readable record mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive, solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable record medium into the one or more storage devices and/or one or more computer processing devices using a drive mechanism. Such separate computer readable record medium may include a universal serial bus (USB) flash drive, a memory stick, a Blu-ray/digital versatile disc (DVD)/compact disc (CD)-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable record medium. Additionally, the computer programs, program code, instructions, or some combination thereof, may be loaded into the one or more storage devices and/or the one or more processors from a remote computing system that is configured to forward and/or distribute the computer programs, program code, instructions, or some combination thereof, over a network. The remote computing system may forward and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Hereinafter, example embodiments will be described with reference to the accompanying drawings.

The example embodiments relate to technology for providing a sign language translation service.

The example embodiments including the disclosures set forth herein may translate audio of a video (e.g., translate speech of speakers in the video call) into sign language in real time using an avatar during a video call.

A sign language translation system according to some example embodiments may be implemented by at least one computing device and a sign language translation method according to some example embodiments may be performed by at least one computing device included in the sign language translation system. A computer program according to an example embodiment may be installed and executed on the computing device and the computing device may perform the sign language translation method according to example embodiments under control of the executed computer program. The aforementioned computer program may be stored in a computer-readable recording medium to computer-implement the sign language translation method in conjunction with the computing device.

FIG. 1 is a diagram illustrating an example of a network environment according to an example embodiment. Referring to FIG. 1, the network environment may include a plurality of electronic devices 110, 120, 130, and 140, a plurality of servers 150 and 160, and a network 170. FIG. 1 is provided as an example. A number of electronic devices or a number of servers is not limited thereto. Also, the network environment of FIG. 1 is provided as one example of environments applicable to the example embodiments and an environment applicable to the example embodiments is not limited to the network environment of FIG. 1.

Each of the plurality of electronic devices 110, 120, 130, and 140 may be a fixed terminal or a mobile terminal that is configured as a computing device. For example, the plurality of electronic devices 110, 120, 130, and 140 may be a smartphone, a mobile phone, a navigation device, a computer, a laptop computer, a digital broadcasting terminal, a personal digital assistant (PDA), a portable multimedia player (PMP), a tablet personal computer (PC), and the like. For example, although FIG. 1 illustrates a shape of a smartphone as an example of the electronic device 110, the electronic device 110 used herein may refer to one of various types of physical computing devices capable of communicating with other electronic devices 120, 130, and 140, and/or the servers 150 and 160 over the network 170 in a wireless or wired communication manner.

The communication scheme is not limited and may include a near field wireless communication scheme between devices as well as a communication scheme using a communication network (e.g., a mobile communication network, wired Internet, wireless Internet, and a broadcasting network) includable in the network 170. For example, the network 170 may include at least one of network topologies that include a personal area network (PAN), a local area network (LAN), a campus area network (CAN), a metropolitan area network (MAN), a wide area network (WAN), a broadband network (BBN), and the Internet. Also, the network 170 may include at least one of network topologies that include a bus network, a star network, a ring network, a mesh network, a star-bus network, a tree or hierarchical network, and the like. However, they are provided as examples only.

Each of the servers 150 and 160 may be configured as a computing device or a plurality of computing devices that provides an instruction, a code, a file, content, a service, etc., through communication with the plurality of electronic devices 110, 120, 130, and 140 over the network 170. For example, the server 150 may be a system that provides a service (e.g., a sign language translation service) to the plurality of electronic devices 110, 120, 130, and 140 connected over the network 170.

Figure 2:
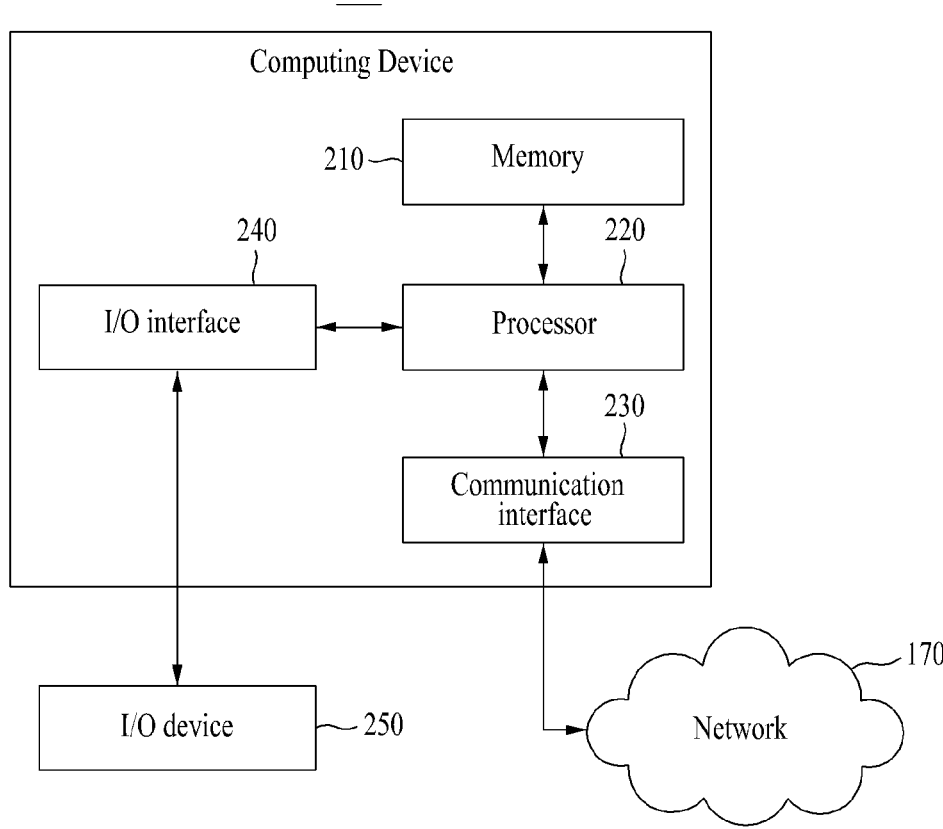
FIG. 2 is a diagram illustrating a configuration of a computing device according to an example embodiment.

FIG. 2 is a diagram illustrating an example of a computing device according to an example embodiment. Each of the plurality of electronic devices 110, 120, 130, and 140 or each of the servers 150 and 160 may be implemented by a computing device 200 of FIG. 2.

Referring to FIG. 2, the computing device 200 may include a memory 210, a processor 220, a communication interface 230, and an input/output (I/O) interface 240. The memory 210 may include a permanent mass storage device, such as a RAM, a ROM, and a disk drive, as a non-transitory computer-readable recording medium. The permanent mass storage device, such as ROM and a disk drive, may be included in the computing device 200 as a permanent storage device separate from the memory 210. Also, an OS and at least one program code may be stored in the memory 210. Such software components may be loaded to the memory 210 from another non-transitory computer-readable recording medium separate from the memory 210. The other non-transitory computer-readable recording medium may include a non-transitory computer-readable recording medium, for example, a floppy drive, a disk, a tape, a DVD/CD-ROM drive, a memory card, etc. According to other example embodiments, software components may be loaded to the memory 210 through the communication interface 230, instead of the non-transitory computer-readable recording medium. For example, the software components may be loaded to the memory 210 of the computing device 200 based on a computer program installed by files received over the network 170.

The processor 220 may be configured to process instructions of a computer program by performing basic arithmetic operations, logic operations, and I/O operations. The computer-readable instructions may be provided by the memory 210 or the communication interface 230 to the processor 220. For example, the processor 220 may be configured to execute received instructions in response to a program code stored in a storage device, such as the memory 210.

The communication interface 230 may provide a function for communication between the computing device 200 and another apparatus, for example, the aforementioned storage devices, through the network 170. For example, the processor 220 of the computing device 200 may deliver a request or an instruction created based on a program code stored in the storage device such as the memory 210, data, and a file, to other apparatuses over the network 170 under control of the communication interface 230. Inversely, a signal, an instruction, data, a file, etc., from another apparatus may be received at the computing device 200 through the communication interface 230 of the computing device 200. For example, a signal, an instruction, data, etc., received through the communication interface 230 may be delivered to the processor 220 or the memory 210, and a file, etc., may be stored in a storage medium, for example, the permanent storage device, further includable in the computing device 200.

The I/O interface 240 may be a device used for interfacing with an I/O device 250. For example, an input device may include a device, such as a microphone, a keyboard, a mouse, etc., and an output device may include a device, such as a display, a speaker, etc. As another example, the I/O interface 240 may be a device for interfacing with a device in which an input function and an output function are integrated into a single function, such as a touchscreen. The I/O device 250 may be configured as a single device with the computing device 200.

Also, according to other example embodiments, the computing device 200 may include a greater or fewer number of components than the number of components of FIG. 2. However, there is no need to clearly illustrate many conventional components. For example, the computing device 200 may be configured to include at least a portion of the I/O device 250 or may further include other components, such as a transceiver and a database.

Hereinafter, example embodiments of a method and apparatus for translating audio of a video into sign language through an avatar are described.

Herein, a video call may inclusively represent a video phone through which video and audio are exchanged between a user and a counterpart, for example, a voice over Internet protocol (VoIP) of technology for converting video and audio into a digital packet through a network using an IP address.

The example embodiments may provide a sign language translation as one of translation options on a VoIP.

The computing device 200 according to the example embodiment may provide a client with a sign language translation service through connection to a dedicated application installed on the client or a website/mobile site related to the computing device 200. A sign language translation system may be configured in the computing device 200 according to the example embodiment. For example, the sign language translation system may be implemented in an independently operating program form or may be configured in an in-app form of a specific application to be operable on the specific application.

The processor 220 of the computing device 200 may be implemented as a component for performing the following sign language translation method. Depending on example embodiments, the components of the processor 220 may be selectively included in or excluded from the processor 220. Also, depending on example embodiments, the components of the processor 220 may be separated or merged for functional representations of the processor 220.

The processor 220 and the components of the processor 220 may control the computing device 200 to perform operations included in the following sign language translation method. For example, the processor 220 and the components of the processor 220 may be implemented to execute an instruction according to a code of at least one program and a code of an OS included in the memory 210.

The components of the processor 220 may be representations of different functions performed by the processor 220 according to an instruction provided from a program code stored in the computing device 200.

The processor 220 may read a necessary instruction from the memory 210 to which instructions related to control of the computing device 200 are loaded. In this case, the read instruction may include an instruction for controlling the processor 220 to perform the following operations.

Operations included in the following sign language translation method may be performed in order different from illustrated order. A portion of operations may be omitted, or an additional process may be further included.

FIG. 3 is a flowchart illustrating an example of a method performed by a computing device according to an example embodiment.

Referring to FIG. 3, in operation S310, the processor 220 may set a sign language translation as one of video call options for each user that desires to participate in a VoIP-based video call. The processor 220 may provide an option to request a translation into sign language (that is a visual language) through environment settings related to a video call, such as a video call entry process, as an option for a specific user (e.g., an option for a user with a hearing impairment).

In operation S320, the processor 220 may set an avatar for sign language expression for each video call participant in the video call in which the sign language translation is set. The avatar may refer to a character that represents a user in a virtual environment and may include a plurality of avatar components. For example, the avatar components may include a component that defines an appearance of the avatar (e.g., an eye shape, a nose shape, a lip shape, a face shape, a body type, a hair style, etc.), a component that defines a gesture of the avatar, and a component that defines an item worn by the avatar (e.g., clothes, shoes, glasses, accessories, etc.). For example, the processor 220 may set an avatar directly selected by a corresponding participant for each video call participant. As another example, the processor 220 may automatically set a non-overlapping avatar through arbitrary settings for each video call participant. When setting an avatar for each video call participant, the processor 220 may recognize a face of each participant in a call video based on a face recognition and artificial intelligence (AI) technology and may generate and use an avatar of a character that resembles a corresponding participant.

In operation S330, the processor 220 may translate audio of a speaker into sign language during the video call. The processor 220 may convert a call audio to a text (e.g., into text data) through a speech-to-text (STT) technique in a VoIP-based video call environment. The processor 220 may convert the converted text into the sign language through an artificial intelligent (AI)-based sign language translation model.

In operation S340, the processor 220 may reproduce a motion corresponding to the sign language translated in operation S330 through an avatar of the corresponding speaker. The processor 220 may express the motion of the avatar that represents the speaker through the motion of the translated sign language. That is, the processor 220 may express a sign language sentence through conversion to preset hand gestures and gestures of other body elements.

The processor 220 may apply an avatar model capable of more naturally expressing the sign language through a lip movement, a facial expression, a complexion, an eye movement, a body movement, and the like in addition to a hand gesture that includes a hand shape, a hand direction, and a hand movement. For example, the processor 220 may apply a facial expression of a speaker extracted in a call video to an avatar model based on face detection technology.

The processor 220 may analyze an emotional state of the corresponding speaker from a spoken sentence or intonation included in the call audio and may apply information on the analyzed emotional state to a facial expression or a gesture of the avatar. In addition to the call audio, the processor 220 may analyze the call video of the speaker based on the face detection technology and may extract an emotional state revealed on a face of the speaker. When providing a sign language translation, the processor 220 may change and express other body gestures, facial expressions, gazes, and postures that may be expressed with the visual language according to an emotion of the speaker in addition to hand gestures of the sign language, through change to various actions of the avatar.

The processor 220 may receive a counterpart video for a video call from a terminal of a counterpart and may display a video call screen that includes a user video and the counterpart video. The processor 220 may configure a video call screen by receiving the counterpart video of the counterpart that participates in the video call as an individual video and then render the received counterpart video with the user video on a single screen.

Also, instead of generating a single video that includes a plurality of participant videos and providing the generated video to a client on the side of the server 150 that provides the video call service, the server 150 may transmit each participant video as an individual video, and the client may receive each of the plurality of participant videos as the individual video and may configure the received individual videos as the video call screen on the single screen.

The server 150 may mix an avatar video that expresses the sign language on one side of the call video and then transmit the same as a participant video or may transmit the call video and the avatar video as individual videos. In a former case, the client may configure the video call screen with the participant video mixed with the avatar video on one side. In a latter case, the client may configure the video call screen by combining the call video and the avatar video according to a defined layout. For example, the client may configure the call video as the video call screen on one screen and may overlay the avatar video translating the sign language on one side (e.g., at a right lower end) of the video call screen.

As an avatar of a different character is set for each video call participant, the processor 220 may provide a sign language translation through a different avatar for each speaker (that is, the avatar set for each speaker).

The processor 220 may apply a separate display element to the video call screen to easily identify the avatar and the participant providing the sign language translation among video call participants, so as to easily identify a speaker of audio that is currently being translated into the sign language.

When at least two participants concurrently speak among the video call participants, the processor 220 may allow avatars of the respective speakers to appear together and may provide a sign language translation for each speaker.

The sign language translation service according to the example embodiment may include a function of translating audio of a speaker into sign language during a video call, as well as a function of recognizing a body gesture of a participant that appears in a call video and providing the recognized body gesture using text or audio. That is, the sign language translation service may translate the sign language (e.g., of a video using captions) by converting the sign language into text based on AI and video recognition technology, or may translate the sign language using audio through a TTS technique.

Figure 4:
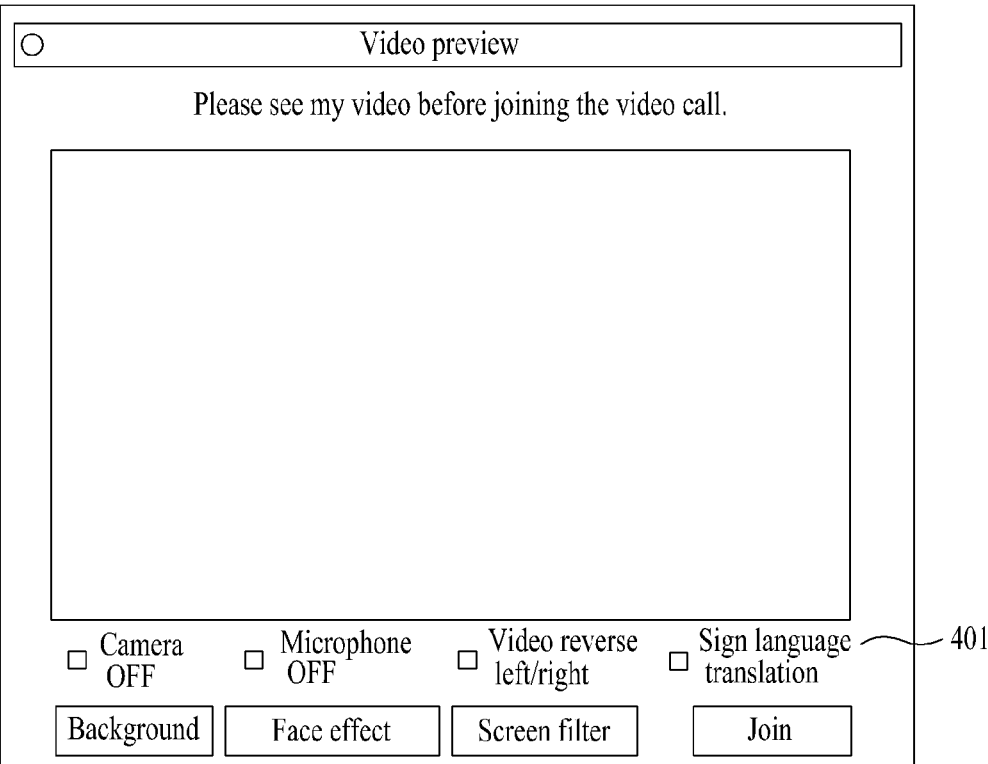
FIG. 4 is a diagram illustrating an example of an interface screen for setting a sign language translation according to an example embodiment.

FIG. 4 is a diagram of an example of an interface screen for setting a sign language translation according to an example embodiment.

FIG. 4 illustrates a setting screen 400 for video call participation.

Referring to FIG. 4, the setting screen 400 may include an interface for various environment settings related to a video call and may include a "sign language translation" menu 401 for setting a sign language translation during the video call.

A user may set the sign language translation for call audio of the user using the "sign language translation" menu 401 prior to participating in the video call.

Figure 5:
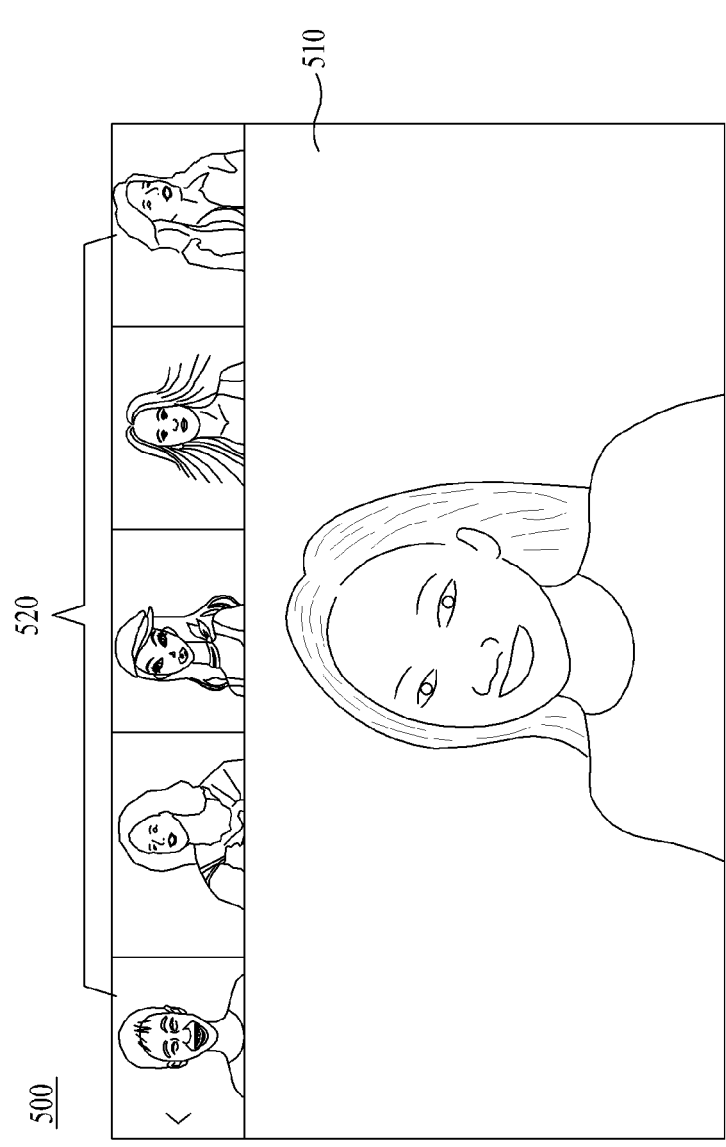
FIGS. 5, 6 and 7 are diagrams illustrating an example of a video call screen for translating audio of a speaker into sign language through an avatar according to an example embodiment.
Figure 6:
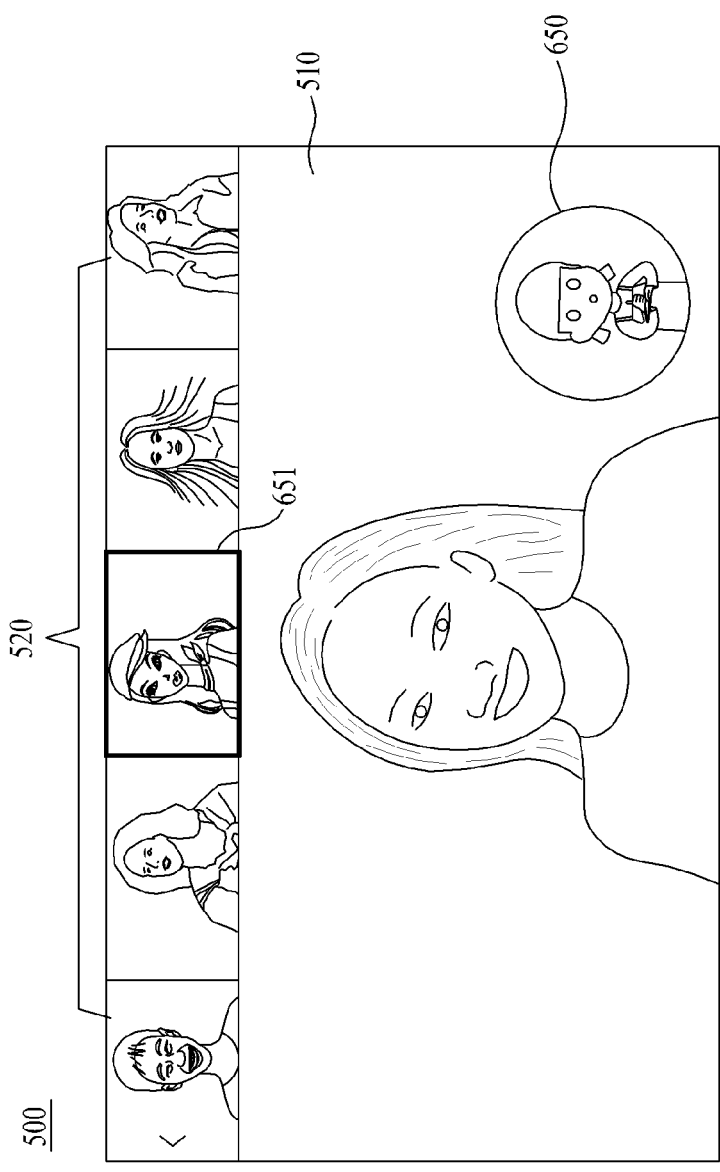
Figure 7:
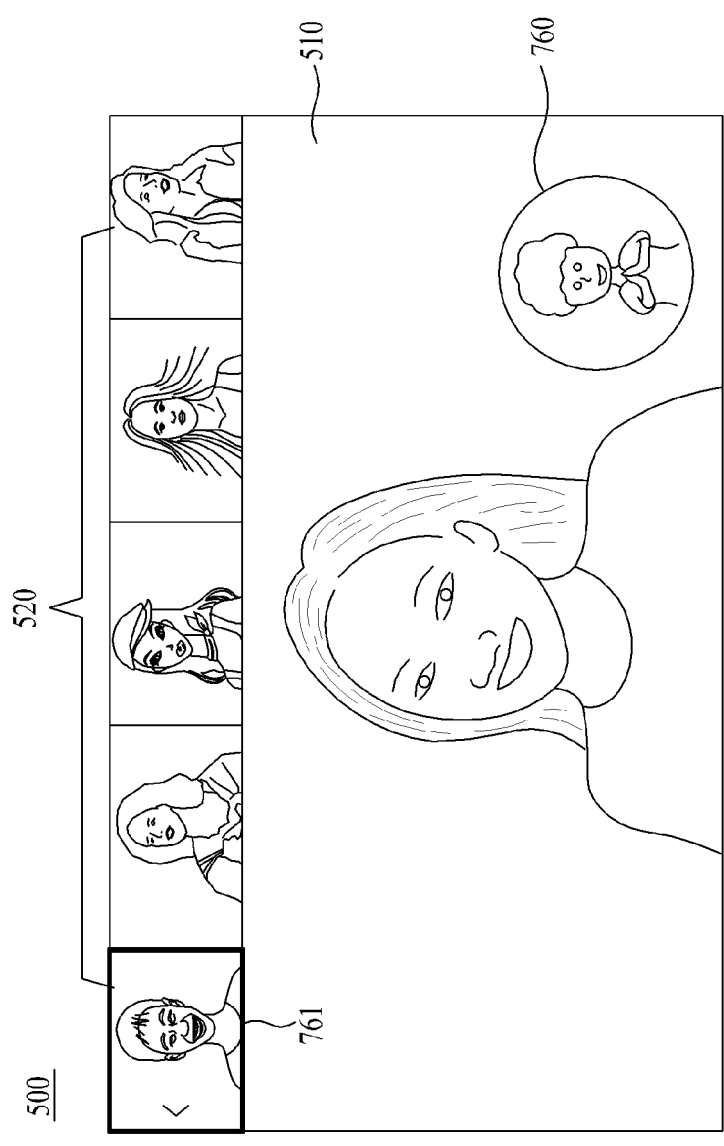

FIGS. 5, 6 and 7 are diagrams illustrating an example of a video call screen for translating audio of a speaker into sign language through an avatar according to an example embodiment.

Referring to FIG. 5, when a user participates in a video call, the processor 220 may receive counterpart videos 520 for the video call from a terminal of each counterpart and may display a video call screen 500 that includes a user video 510 and the counterpart videos 520.

The processor 220 may configure the video call screen 500 by receiving the counterpart video 520 of each participant that participates in the video call as an individual video and by rendering the received counterpart videos 520 with the user video 510 on a single screen.

Referring to FIG. 6, the processor 220 may translate call audio into sign language during the video call. The processor 220 may provide a sign language translation for audio of a corresponding speaker using an avatar 650 corresponding to the speaker.

The server 150 may transmit a call video of each participant as an individual video and may also provide a video of the avatar 650 providing the sign language translation. The processor 220 may display the video of the avatar 650 to be overlaid on the video call screen 500 on which the user video 510 and the counterpart video 520 are rendered on a single screen.

The processor 220 may display which avatar among the avatars of video call participants (or which call participant in embodiments were the counterpart videos 520 are not using avatars) corresponds to the avatar 650. That is, the processor 220 may identify, via a visual effect, a speaker of audio that is currently being translated into the sign language such that the speaker of the audio is distinguished from other partici-pants through a separate display element 651 on the video call screen 500.

Although FIG. 6 illustrates the avatar 650 at a right lower end of the video call screen 500, the avatar 650 according to another embodiment may be displayed to be adjacent to a video of the corresponding speaker, may be displayed to be overlaid in the video of the speaker, or may be displayed instead of the video of the speaker within the counterpart video 520.

Referring to FIG. 7, when a speaker is switched during the video call, the processor 220 may display a current speaker to be distinguished from other participants through a display element 761 and, at the same time, translate call audio into the sign language using an avatar 760 of the current speaker.

That is, the processor 220 may provide the sign language translation through the respective different avatars 650 and 760 according to the respective corresponding speakers, such that the speakers may be easily distinguished from each other.

Figure 8:
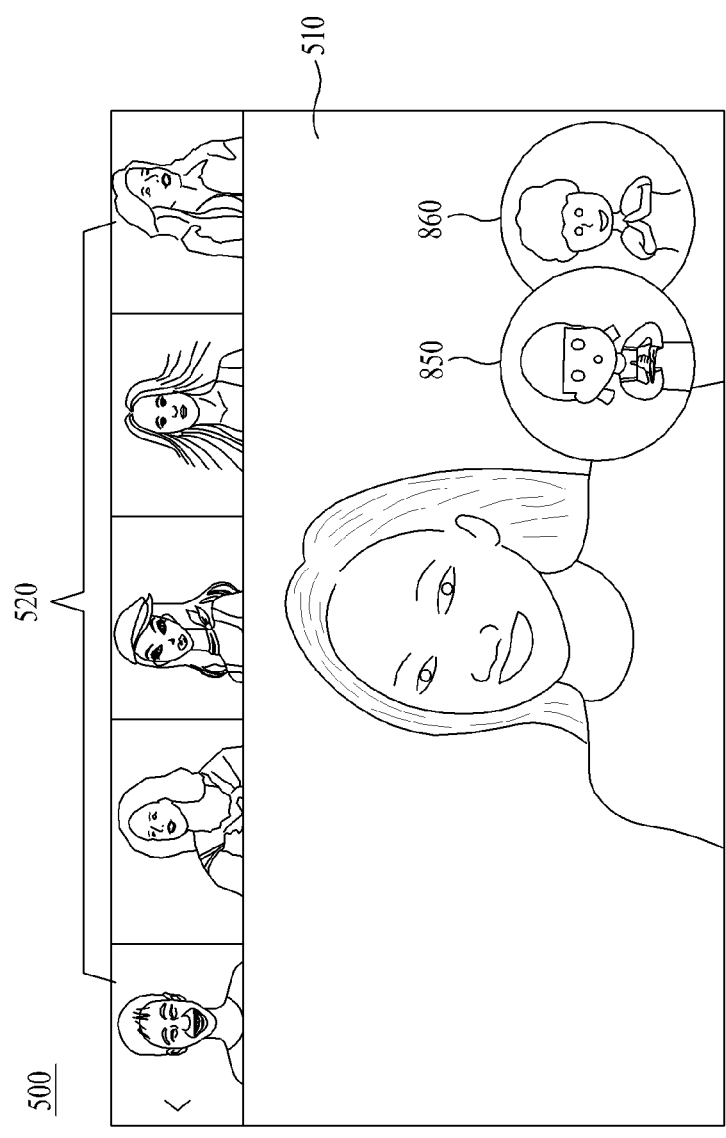
FIGS. 8 and 9 are diagrams illustrating an example of a video call screen for translating audio concurrently spoken by a plurality of speakers into sign language according to an example embodiment.
Figure 9:
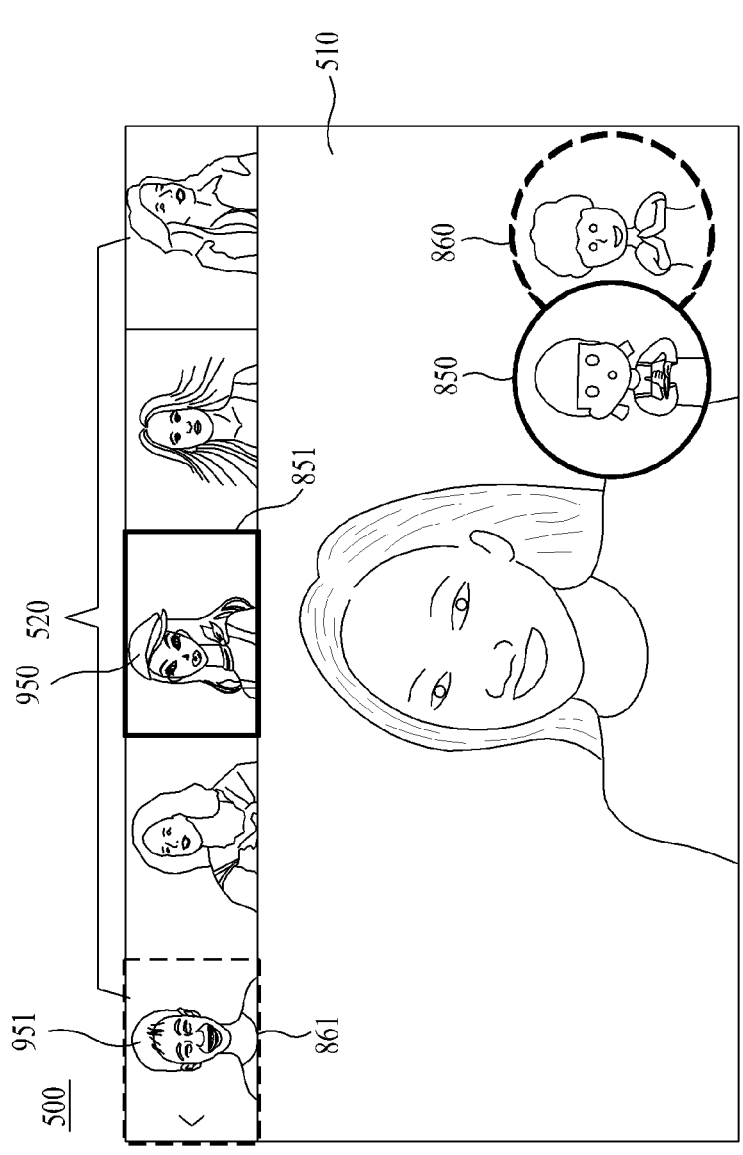

FIGS. 8 and 9 are diagrams of an example of a video call screen for translating audio concurrently spoken by a plu-rality of speakers into sign language according to an example embodiment.

Referring to FIG. 8, when at least two participants con-currently speak among video call participants, the processor 220 may allow avatars 850 and 860 of the respective speakers to appear together on the video call screen 500 and may provide sign language translation for each speaker through the avatars 850 and 860.

Referring to FIG. 9, to easily identify a speaker in a concurrent speaking environment, the processor 220 may differently display corresponding display elements 851 and 861 of call videos between the speakers to be distinguished from each other. The processor 220 may unify some of display elements of the avatars 850 and 860 with the display elements 851 and 861 of the call videos for the respective speakers.

For example, when user A 950 and user B 951 concur-rently speak, the processor 220 may apply a solid line outline to a call video and an avatar of user A 950 and may apply a dashed line outline to a call video and an avatar of user B 951. In other embodiments, the processor 220 may apply color effects, video effects or other effects such that a visual effect that is applied to a counterpart video being displayed corresponds to a visual effect that is applied to the avatar (and/or the avatar video being displayed). Therefore, a sign language translation for audio spoken by each of user A 950 and user B 951 may be easily identified and recog-nized.

FIG. 9 illustrates only an avatar of a user who is speaking. According to another example embodiment, an avatar of each user may be displayed to be overlaid on the counterpart video 520 for a video call to which the sign language translation is set. An avatar for a speaker may be displayed using a different size or color to be distinguished from an avatar of another user.

Figure 10:
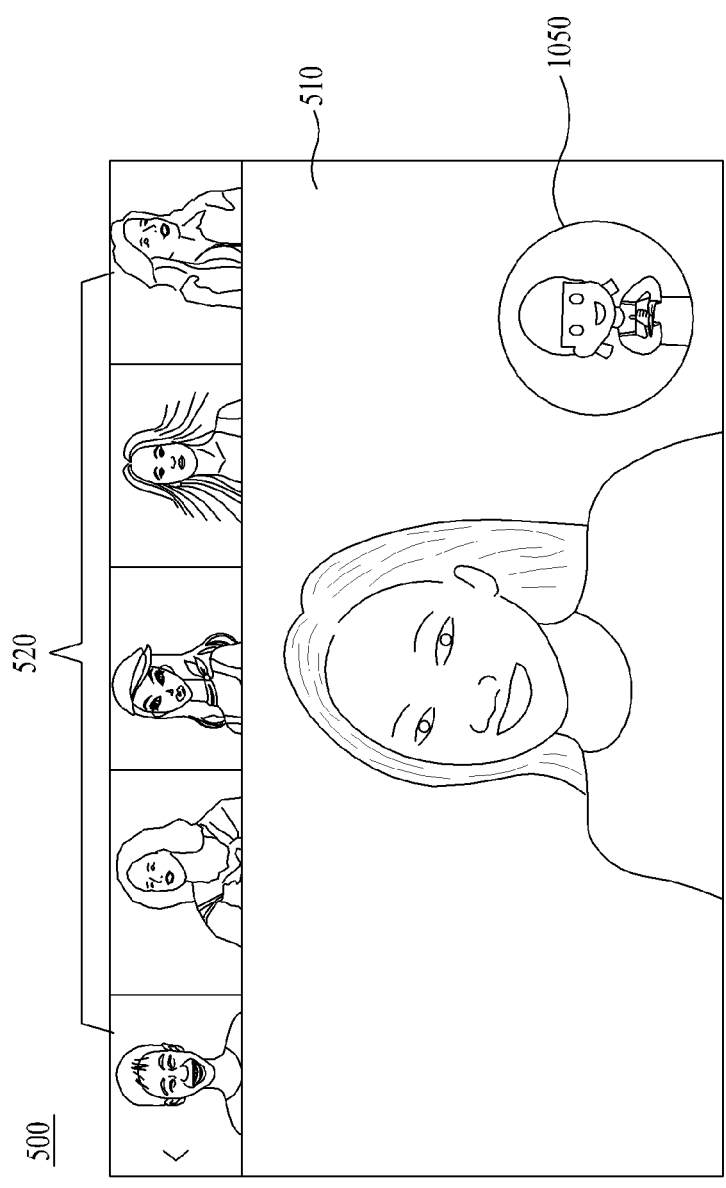
FIG. 10 is a diagram illustrating an example of a sign language translation avatar to which an emotion of a speaker is applied according to an example embodiment.

FIG. 10 is a diagram illustrating an example of a sign language translation avatar to which an emotion of a speaker is applied according to an example embodiment.

When an avatar 1050 corresponding to a speaker appears on the video call screen 500 and, in response thereto, the processor 220 provides a sign language translation for audio of the corresponding speaker, the processor 220 may analyze a current emotional state of the speaker from a call video of the speaker, a sentence or intonation of the speaker, and the like, and may apply information on the analyzed emotional state to a facial expression or a gesture of the avatar 1050.

Referring to FIG. 10, when the speaker speaks "thank you" while smiling during a video call, the processor 220 may extract an emotional state "joy" from the call video or speaking content and, may express a facial expression of the avatar 1050 as a simile expression that represents the emotional state "joy."

Figure 11:
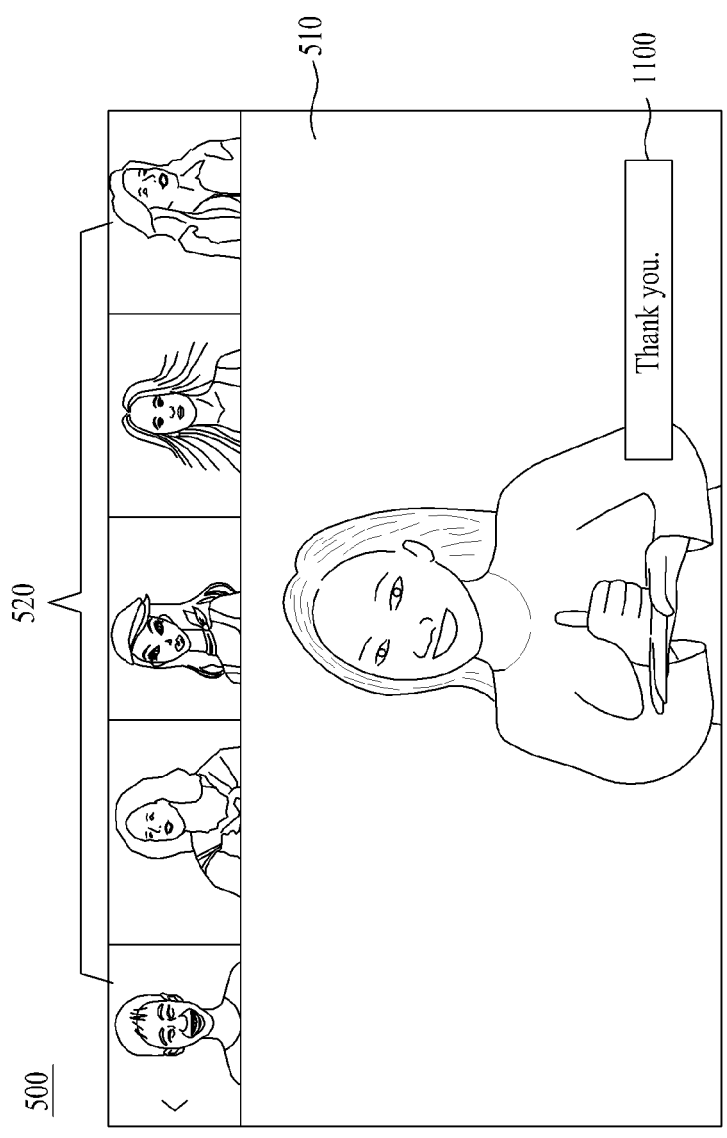
FIG. 11 is a diagram illustrating an example of a video call screen for translating sign language recognized in a video into caption according to an example embodiment.

FIG. 11 is a diagram illustrating an example of a video call screen for translating sign language recognized in a video into caption according to an example embodiment.

The processor 220 may translate call audio into sign language and may also translate the sign language of a call video into text or audio during a video call.

Referring to FIG. 11, when a user uses the sign language during the video call, the processor 220 may recognize a sign language motion expressed by the user from the user video 510, may translate the recognized sign language into text, and may provide text caption 1100 as a sign language translation result. Thee processor 220 may provide the text caption 1100 while applying a facial expression or a gesture corresponding to the sign language or the converted text to the avatar using the avatar of the user using the sign language.

The processor 220 may provide a translation result for sign language of a video as the text caption 1100 and may also provide the translation result in a form of audio through TTS.

Although the example embodiments are described to provide a sign language translation service during a video call, it is provided as an example only and the sign language translation service may be applied to any video-based ser-vice capable of delivering visual information. For example, in a video platform that shares video content, audio of a character that appears in a video may be translated into sign language using an avatar during playback of the video. By setting an avatar of a different character for each character, audio of a corresponding character may be translated into sign language through an avatar of the corresponding char-acter.

According to some example embodiments, to the system may translate audio of a video into sign language in real time using an avatar during a video call. According to some example embodiments, to the system or user may easily identify a speaking entity by providing sign language through an avatar of each speaker. According to some example embodiments, the system may analyze emotion of a speaker from a call video or a call audio and apply the analyzed emotion to a facial expression of an avatar that provides the sign language translation.

The apparatuses described above may be implemented using hardware components, software components, and/or a combination thereof. For example, the apparatuses and components described herein may be implemented using one or more general-purpose or special purpose computers, for example, a processor, a controller, an ALU, a digital signal processor, a microcomputer, a FPGA, a program-mable logic unit (PLU), a microprocessor, or any other device capable of responding to and executing instructions in a defined manner. A processing device may run an OS and one or more software applications that run on the OS. The processing device also may access, store, manipulate, pro-cess, and create data in response to execution of the soft-ware. For simplicity, the description of a processing device is used as singular; however, one skilled in the art will be appreciated that the processing device may include multiple processing elements and/or multiple types of processing elements. For example, the processing device may include multiple processors or a processor and a controller. In addition, different processing configurations are possible, such as parallel processors.

The software may include a computer program, a piece of code, an instruction, or some combinations thereof, for independently or collectively instructing or configuring the processing device to operate as desired. Software and/or data may be embodied in any type of machine, component, physical equipment, a computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more computer readable storage mediums.

The methods according to some example embodiments may be configured in a form of program instructions performed through various computer methods and recorded in non-transitory computer-readable media. The media may include, alone or in combination with program instructions, data files, data structures, and the like. The media may continuously store computer-executable programs or may temporarily store the same for execution or download. Also, the media may be various types of recording devices or storage devices in a form in which one or a plurality of hardware components are combined. Without being limited to media directly connected to a computer system, the media may be distributed over the network. Examples of the media include magnetic media such as hard disks, floppy disks, and magnetic tapes; optical media such as CD-ROM and DVDs; magneto-optical media such as floptical disks; and hardware devices that are specially configured to store and perform program instructions, such as ROM, RAM, flash memory, and the like. Examples of other media may include recording media and storage media managed by an app store that distributes applications or a site, a server, and the like that supplies and distributes other various types of software.

The foregoing embodiments are merely examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A sign language translation method performed by at least one processor, the sign language translation method comprising:
setting a sign language translation avatar for each participant among a plurality of participants of a video call;
translating speech of at least one speaker into sign language during the video call, the at least one speaker being at least one participant among the plurality of participants who is speaking during the video call; and
displaying the sign language through the sign language translation avatar of the at least one speaker during the video call,
wherein the displaying comprises displaying an avatar video corresponding to the sign language translation avatar of the at least one speaker to be overlaid on a video call screen including a call video of the each participant, and wherein, in the call video, avatar videos of the participants other than the at least one speaker who are not currently speaking are not displayed, and a display element visually indicating that the at least one speaker is currently speaking is displayed in association with a call video of the at least one speaker.

2. The sign language translation method of claim 1, further comprising providing a video call option for selecting sign language translation for each participant of the video call,
wherein the setting is performed based on a selection of the video call option for sign language translation.

3. The sign language translation method of claim 1, wherein the setting comprises:
recognizing a face from a call video of at least one participant of the video call,
generating a first avatar based on the recognized face, and
setting the first avatar as the sign language translation avatar.

4. The sign language translation method of claim 1, wherein the translating the speech of the at least one speaker into sign language comprises analyzing an emotional state of the at least one speaker from at least one of the call video and a call audio of the at least one speaker; and
wherein the method further comprises representing the emotional state of the at least one speaker with a facial expression or a gesture of the sign language translation avatar.

5. The sign language translation method of claim 1, wherein the at least one speaker comprises at least two speakers,
wherein avatars of the at least two speakers appear together in the video call, and
wherein translating the speech of the at least one speaker into sign language comprises translating speech of each of the at least two speakers into sign language when the at least two speakers concurrently speak.

6. The sign language translation method of claim 1, wherein the displaying comprises:
in a case where two or more participants among the plurality of participants are speaking simultaneously,
displaying a first display element indicating that a first participant among the two or more participants is currently speaking, in association with a call video of the first participant, and displaying a second display element, visually distinguishable from the first display element, indicating that a second participant is currently speaking, in association with a call video of the second participant; and
displaying a first common element in association with an avatar video corresponding to the sign language translation avatar of the first participant, the first common element including a visual element in common with the first display element, and displaying a second common element in association with an avatar video corresponding to the sign language translation avatar of the second participant, the second common element including a visual element in common with the second display element.

7. The sign language translation method of claim 1, further comprising:
recognizing sign language in a call video during the video call; and
translating the recognized sign language into a text caption or audio.

8. A computing device comprising:

a memory storing instructions; and at least one processor configured to execute the instructions to:

set a sign language translation avatar for each participant among a plurality of participants of a video call; and translate speech of at least one speaker into sign language during the video call, the at least one speaker being at least one participant among the plurality of participants who is speaking during the video call; and display the sign language through the sign language translation avatar of the at least one speaker during the video call, wherein the at least one processor is configured to display the sign language by displaying an avatar video corresponding to the sign language translation avatar of the at least one speaker to be overlaid on a video call screen including a call video of the each participant, and wherein, in the call video, avatar videos of the participants other than the at least one speaker who are not currently speaking are not displayed, and a display element visually indicating that the at least one speaker is currently speaking is displayed in association with a call video of the at least one speaker.

9. The computing device of claim 8, wherein the at least one processor is further configured to execute the instructions to:

provide a video call option for selecting sign language translation for each participant of the video call, wherein the setting of the sign language translation avatar is performed based on a selection of the video call option for sign language translation.

10. The computing device of claim 8, wherein the at least one processor is further configured to execute the instructions to:

recognize a face from a call video of at least one participant of the video call, generate a first avatar based on the recognized face, and set the first avatar as the sign language translation avatar.

11. The computing device of claim 8, wherein the at least one processor is further configured to execute the instructions to:

analyze an emotional state of the at least one speaker from at least one of the call video and a call audio of the at least one speaker, and represent the emotional state of the at least one speaker with a facial expression or a gesture of the sign language translation avatar.

12. The computing device of claim 8, wherein the at least one speaker comprises at least two speakers, wherein avatars of the at least two speakers appear together in the video call, and wherein the at least one processor is further configured to execute the instructions to translate speech of each of the at least two speakers into sign language when the at least two speakers concurrently speak.

13. The computing device of claim 8, wherein, in a case where two or more participants among the plurality of participants are speaking simultaneously, the at least one processor is configured to display a first display element indicating that a first participant among the two or more participants is currently speaking, in association with a call video of the first participant, and display a second display element, visually distinguishable from the first display element, indicating that a second participant is currently speaking, in association with a call video of the second participant; and display a first common element in association with an avatar video corresponding to the sign language translation avatar of the first participant, the first common element including a visual element in common with the first display element, and display a second common element in association with an avatar video corresponding to the sign language translation avatar of the second participant, the second common element including a visual element in common with the second display element.

14. The computing device of claim 8, wherein the at least one processor is further configured to execute the instructions to:

recognize sign language in a call video during the video call, and translate the recognized sign language into a text caption or audio.

\* \* \* \* \*